(12) United States Patent
Schmitz et al.

(10) Patent No.: US 10,864,321 B1
(45) Date of Patent: Dec. 15, 2020

(54) JOINT CAPSULE FLUID DELIVERY DEVICE

(71) Applicants: Thomas Leroy Schmitz, Woodbury, MN (US); Jesse James Corry, Woodbury, MN (US)

(72) Inventors: Thomas Leroy Schmitz, Woodbury, MN (US); Jesse James Corry, Woodbury, MN (US)

( * ) Notice: Subject to any disclaimer, the term of this patent is extended or adjusted under 35 U.S.C. 154(b) by 0 days.

(21) Appl. No.: 16/739,816

(22) Filed: Jan. 10, 2020

Related U.S. Application Data

(63) Continuation of application No. 16/695,153, filed on Nov. 25, 2019.

(51) Int. Cl.
*A61M 5/168* (2006.01)
*A61M 5/142* (2006.01)
(Continued)

(52) U.S. Cl.
CPC ........ *A61M 5/16813* (2013.01); *A61M 1/008* (2013.01); *A61M 5/1452* (2013.01); *A61M 5/14228* (2013.01); *A61M 5/158* (2013.01); *A61M 2202/0415* (2013.01); *A61M 2202/0468* (2013.01); *A61M 2202/0494* (2013.01); *A61M 2202/08* (2013.01); *A61M 2202/09* (2013.01);
(Continued)

(58) Field of Classification Search
CPC .......... A61M 5/16804; A61M 5/16813; A61M 5/16836; A61M 5/14212; A61M 5/14228; A61M 1/00; A61M 1/0023; A61M 1/008; A61M 1/0088; A61M 2205/3331; A61M 2205/3334; A61M 27/00
See application file for complete search history.

(56) References Cited

U.S. PATENT DOCUMENTS 5,164,597 A * 11/1992 Lodder ................. G01N 21/51
250/228
5,378,233 A * 1/1995 Haber ..................... A61M 5/19
604/135
(Continued)

OTHER PUBLICATIONS

Ateschrang, A., Albrecht, D., Schröter, S., Hirt, B., Weise, K., & Dolderer, J. H., Septic arthritis of the knee: presentation of a novel irrigation-suction system tested in a cadaver studym, 2011, BMC musculoskeletal disorders, 12, 180. doi: 10.1186/1471-2474-12-180 (Year: 2011).*

(Continued)

*Primary Examiner* — Kevin C Sirmons
*Assistant Examiner* — Tezita Z Watts
(74) *Attorney, Agent, or Firm* — Lund IP, PLLC (57) ABSTRACT

An external medical device includes a fluid inlet, an inlet valve in fluid communication with the fluid inlet to control fluid flow through the fluid inlet in response to fluid inlet control signals, a fluid outlet in fluid communication with a fluid reservoir, a fluid pump configured to deliver a therapeutic fluid from the fluid reservoir through the fluid outlet in response to fluid outlet control signals, a fluid sensor configured to monitor the therapeutic fluid between the fluid pump and the fluid outlet and further configured to output sensor data corresponding to a monitored condition of the therapeutic fluid, and a control module configured to receive the sensor data and output, based on the sensor data, the fluid inlet control signals to the inlet valve and the fluid outlet control signals to the fluid pump.

22 Claims, 6 Drawing Sheets

(51) Int. Cl.
*A61M 5/158* (2006.01)
*A61M 1/00* (2006.01)
*A61M 5/145* (2006.01)

(52) U.S. Cl.
CPC .............. *A61M 2205/0238* (2013.01); *A61M 2205/051* (2013.01); *A61M 2205/052* (2013.01); *A61M 2205/3306* (2013.01); *A61M 2205/3334* (2013.01); *A61M 2205/3344* (2013.01); *A61M 2205/50* (2013.01); *A61M 2205/75* (2013.01); *A61M 2205/8206* (2013.01); *A61M 2210/02* (2013.01)

(56) References Cited

U.S. PATENT DOCUMENTS

| | | | | |
|---|---|---|---|---|
| 5,382,229 | A * | 1/1995 | Grabenkort | A61M 1/0058 604/27 |
| 6,024,720 | A * | 2/2000 | Chandler | A61M 1/0058 604/35 |
| 6,325,788 | B1 * | 12/2001 | McKay | A61M 1/0005 604/120 |
| 7,771,716 | B2 | 8/2010 | Hedrick et al. | |
| 2004/0256329 | A1 * | 12/2004 | Meserol | A61M 1/3683 210/748.09 |
| 2006/0051396 | A1 * | 3/2006 | Hamilton | A61L 27/227 424/423 |
| 2012/0123360 | A1 * | 5/2012 | Locke | A61M 1/0023 604/319 |
| 2015/0025311 | A1 * | 1/2015 | Kadan | A61B 1/015 600/104 |
| 2020/0046888 | A1 * | 2/2020 | Locke | A61M 1/0084 |

OTHER PUBLICATIONS

Arthrex Inc ,DualWave™ Pump Operation, 2017, https://www.arthrex.com/resources/animation/3RnF2R5CN0-AeQFS-g07XA/dualwave-pump-operation (Year: 2017).*

Ateschrang, A., Albrecht, D., Schroter, S., Hirt, B., Weise, K., & Dolderer, J. H., Septic arthritis of the knee: presentation of a novel irrigation-suction system tested in a cadaver studym, Aug. 7, 2011 (Year: 2011).*

Arthrex Inc .DualWave™ Pump Operation, 2017, https://www.arthrex.com/resources/animation/3RnF2R5CN0-AeGFS-g07XA/dualwave-pump-operation (Year: 2017).*

"Pump." Dictionary.com, 2011. (Year: 2011).*
"Valve." Dictionary.com, 2011. (Year: 2011).*

Ateschrang et al., Septic arthritis of the knee: Presentation of a novel irrigation-suction system tested in a cadaver study, BMC Musculoskeletal Disorders, Aug. 7, 2011, Germany.

Hamblin, Can osteoarthritis be treated with light?, Arthritis Research & Therapy, Oct. 29, 2013, Germany.

Khoo et al., Bedside Continuous Irrigation and Drainage as an Interim Local Treatment for Septic Arthritis of the Knee in the Medically Unstable Patient: A Case Report, Malaysian Orthopaedic Journal, Jun. 2015, Malaysia.

* cited by examiner

JOINT CAPSULE FLUID DELIVERY DEVICE

RELATED APPLICATION

This application is a continuation application of U.S. patent application Ser. No. 16/695,153, titled JOINT CAPSULE FLUID DELIVERY, filed Nov. 25, 2019, the entire contents of which are incorporated by reference herein.

TECHNICAL FIELD

This disclosure relates to external medical devices.

BACKGROUND

Synovial joints include connective tissue structures that enclose a joint capsule the joint. A fibrous layer seals the bones of the joint and joint capsule is filled with synovial fluid. Most joints of a mammal are synovial joints, including hinge joints, such as elbow, knee, ankle, and interphalangeal joints, ball-and-socket joints, such as hip and shoulder joints, condyloid joints, such as metacarpophalangeal joints of the fingers and radiocarpal joint of the wrist, facet joints, such as vertebral joints, and others.

Injuries to tissues within joint capsules are generally slow to heal. For example, the lack of blood flow within a joint capsule limits natural healing supported by blood flow, such the delivery of oxygen and nutrients. For this reason, damaged and degraded tissues within a joint capsule are often represent chronic injuries. Such injuries include partially and completely torn ligaments, torn or worn meniscus, worn cartilage, and arthritis.

Such injuries may require surgical intervention and/or lifetime management, such as physical therapy and pain management techniques. However, even in the case of surgical intervention to tissues within a joint capsule, healing times are often measured in months or even years, significantly longer recovery periods than are common with soft tissue injuries in which blood flow supports natural healing.

BRIEF SUMMARY

This disclosure is directed to techniques for delivering therapeutic fluid to a joint capsule of a patient. The disclosed techniques include a portable joint capsule fluid delivery device, which facilitates long term treatment of a joint capsule with a therapeutic fluid. Also disclosed are techniques for delivery of therapeutic fluids to joint capsules to aid in rejuvenation and healing. In various examples, such therapeutic fluids may include stem cells, blood or components thereof, such as platelet-rich plasma, micro-fragmented adipose tissue, Wharton's jelly, saline or other irrigation fluid, antiseptic fluids and others. In some examples, treatment may include circulating therapeutic fluid through the joint capsule and, optionally, reconditioning circulated fluid within a portable joint capsule fluid delivery device. Such reconditioning may include filtering and/or light exposure, which may activate mitochondrial respiration and adenosine triphosphate (ATP) production within living cells of the therapeutic fluid.

In one example, this disclosure is directed to an external medical device including a fluid inlet, an inlet valve in fluid communication with the fluid inlet to control fluid flow through the fluid inlet in response to fluid inlet control signals, a fluid outlet in fluid communication with a fluid reservoir, a fluid pump configured to deliver a therapeutic fluid from the fluid reservoir through the fluid outlet in response to fluid outlet control signals, a fluid sensor configured to monitor the therapeutic fluid between the fluid pump and the fluid outlet and further configured to output sensor data corresponding to a monitored condition of the therapeutic fluid, and a control module configured to receive the sensor data and output, based on the sensor data, the fluid inlet control signals to the inlet valve and the fluid outlet control signals to the fluid pump.

In another example, this disclosure is direct to a method for delivering fluid to a joint capsule of a patient. The method includes pumping a therapeutic fluid with a fluid pump of an external medical device via a fluid outlet of the external medical device into the joint capsule of the patient via a first tubing segment, controlling flow from the joint capsule of the patient via a second tubing segment with an inlet valve of the external medical device via a fluid inlet of the external medical device, monitoring a condition of the therapeutic fluid between the fluid pump and the fluid outlet with a fluid sensor of the external medical device, transmitting sensor data based on the monitored condition of the therapeutic fluid from the fluid sensor to a control module of the external medical device, and based on the sensor data, sending fluid inlet control signals to the inlet valve and the fluid outlet control signals to the fluid pump with the control module to circulate the therapeutic fluid through the joint capsule of the patient according to preprogrammed flow rates while maintaining a positive fluid pressure within the joint capsule of the patient.

In a further example, this disclosure is directed to an external medical device including a fluid reservoir, a fluid outlet in fluid communication with the fluid reservoir, a fluid pump configured to deliver a therapeutic fluid from the fluid reservoir through the fluid outlet in response to fluid outlet control signals, a fluid inlet, an inlet valve in fluid communication with the fluid inlet and the fluid reservoir, the inlet valve being configured to control fluid flow through the fluid inlet to replenish the fluid reservoir in response to fluid inlet control signals, a fluid filter within a flow path between the fluid inlet and the fluid outlet, a fluid sensor configured to monitor the therapeutic fluid between the fluid pump and the fluid outlet and further configured to output sensor data corresponding to a monitored condition of the therapeutic fluid, a control module configured to receive the sensor data and output, based on the sensor data, the fluid inlet control signals to the inlet valve and the fluid outlet control signals to the fluid pump, a first tubing segment in fluid communication with the fluid outlet, a first needle in fluid communication with the first tubing segment, the first needle being configured to access a joint capsule of a patient to facilitate infusing the joint capsule with the therapeutic fluid via the fluid outlet and the first tubing segment, a second tubing segment in fluid communication with the fluid inlet, and a second needle in fluid communication with the second tubing segment, the second needle being configured to access the joint capsule of the patient to facilitate draining the joint capsule via the second tubing segment and the fluid inlet.

DETAILED DESCRIPTION

Figure 1A:
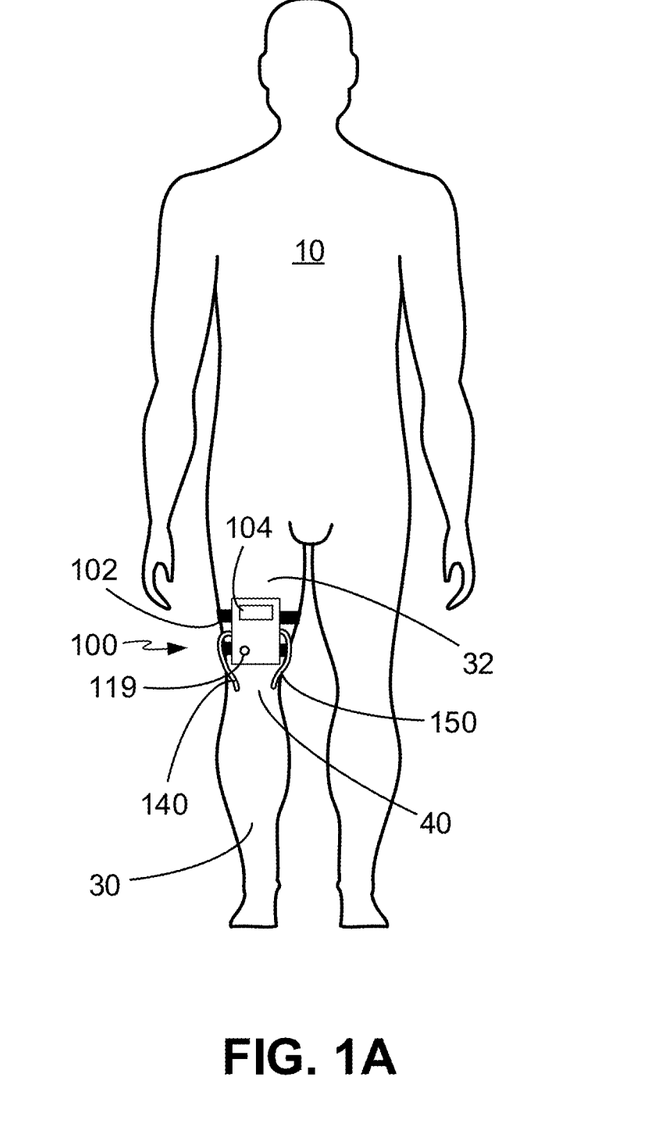
FIG. 1A is a conceptual diagram of a human patient receiving treatment to their right knee with a portable joint capsule fluid delivery device.
Figure 1B:
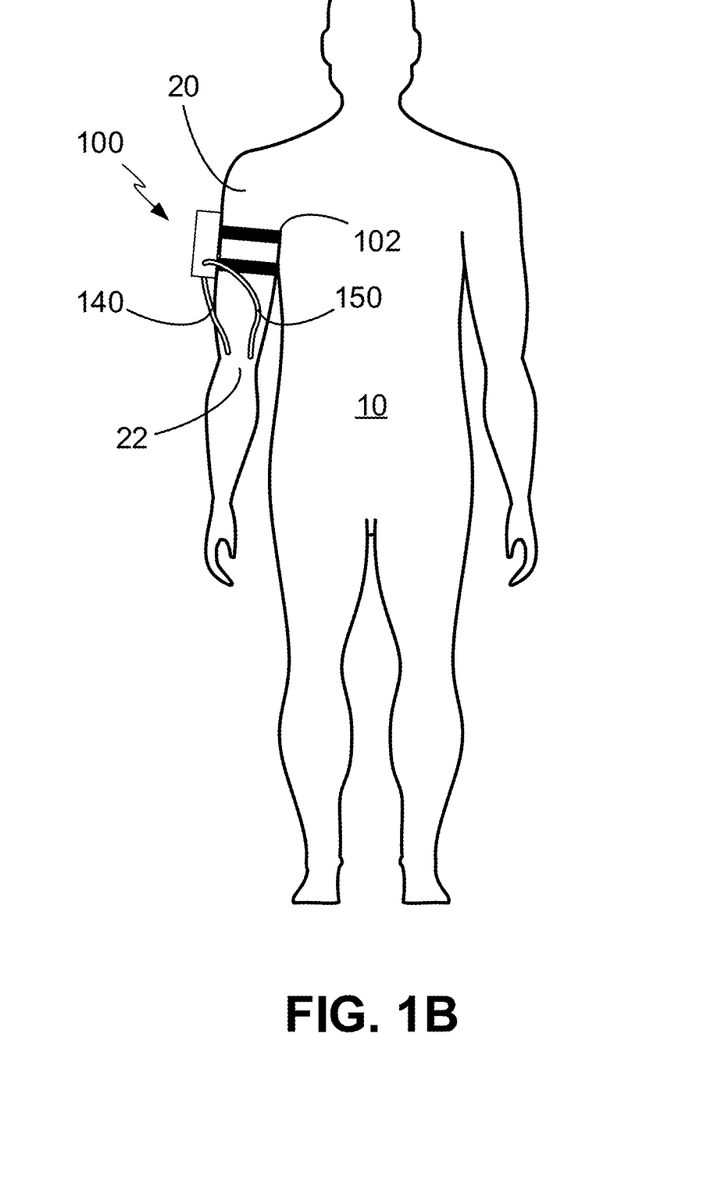
FIG. 1B is a conceptual diagram of a human patient receiving treatment to their left elbow with a portable joint capsule fluid delivery device.
Figure 2:
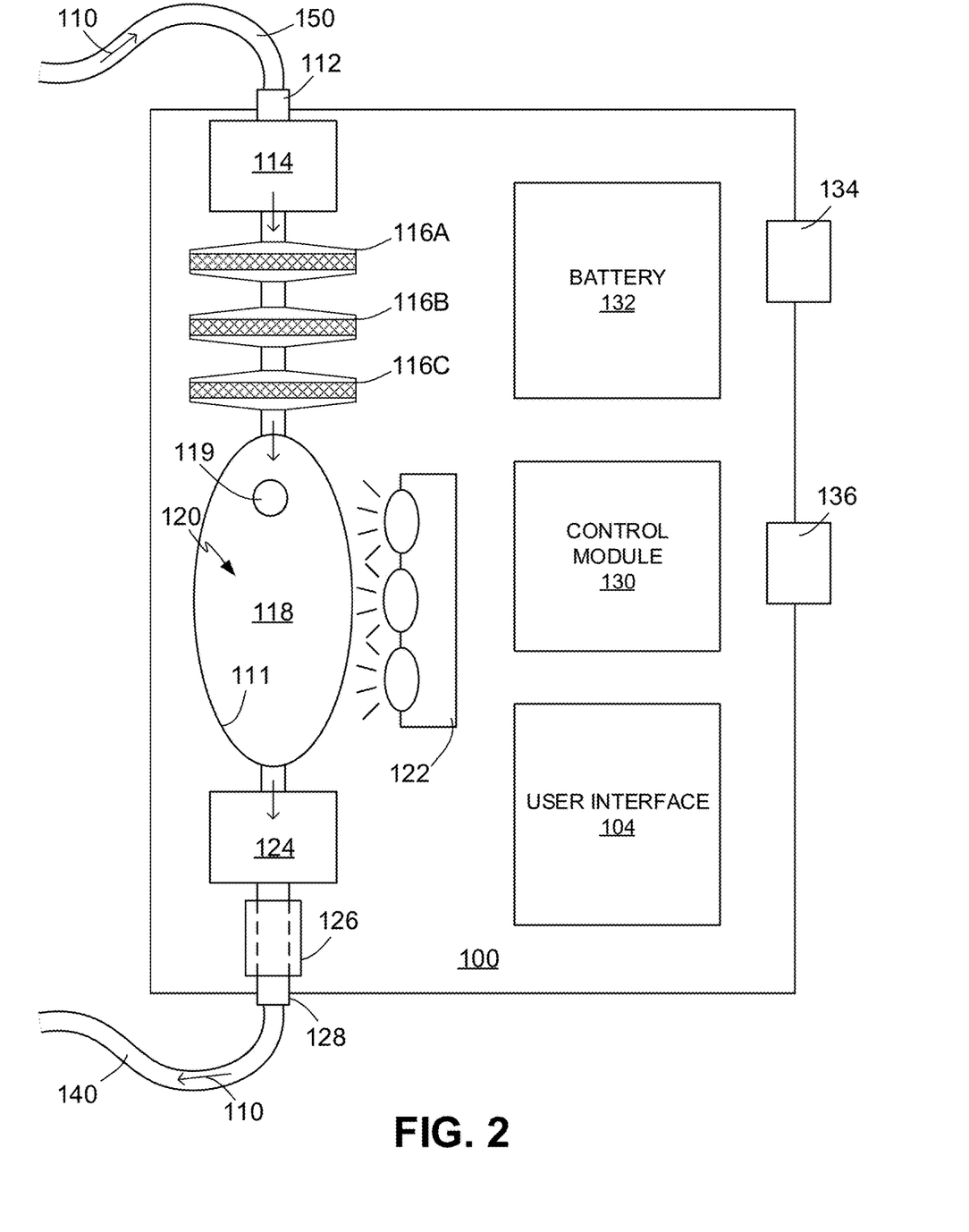
FIG. 2 is a conceptual block diagram of a portable joint capsule fluid delivery device.
Figure 3:
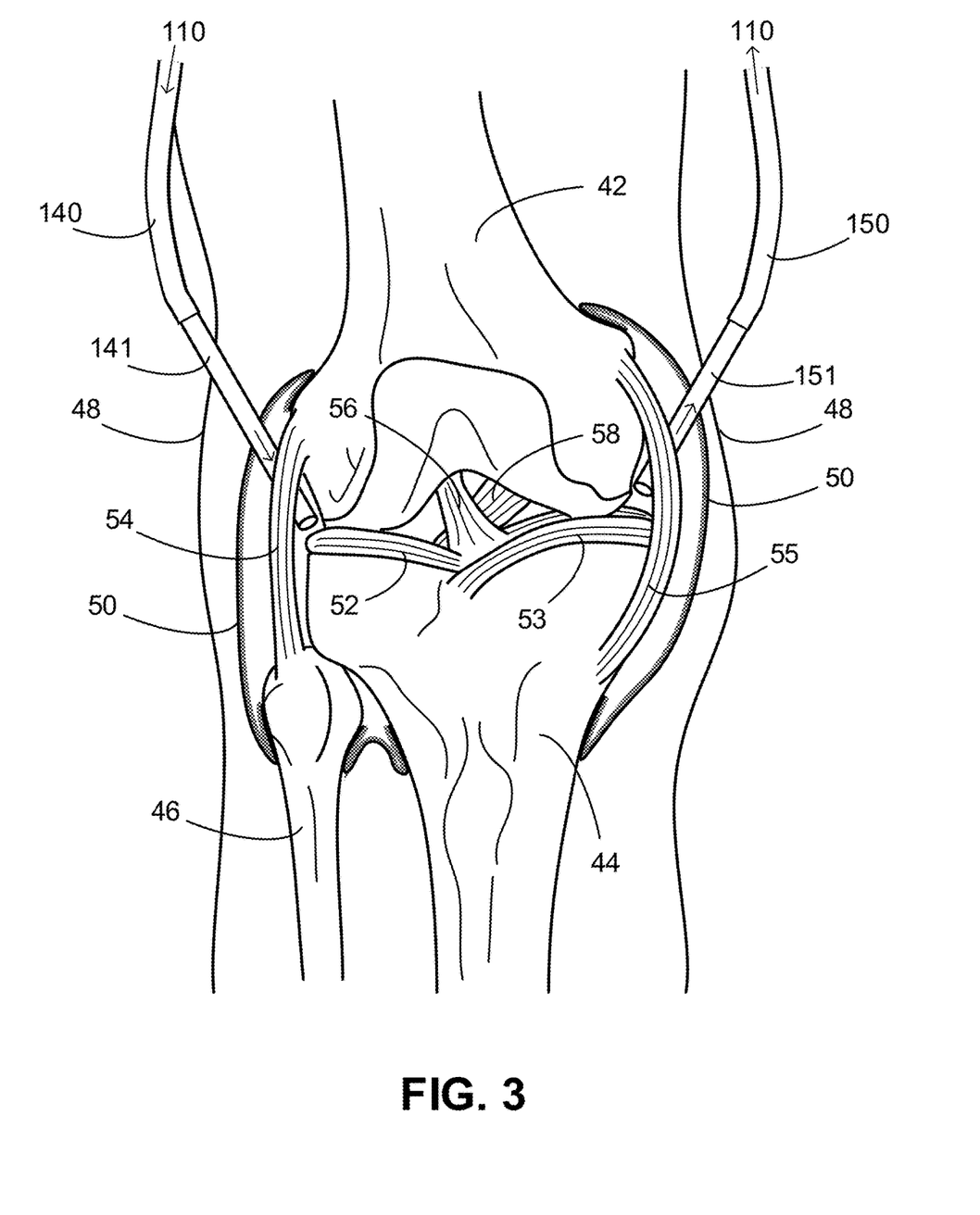
FIG. 3 is an anatomical illustration of a knee of a patient receiving treatment with a portable joint capsule fluid delivery device.

FIG. 1A is a conceptual diagram of a human patient 10 receiving treatment to their right knee 40 with a portable joint capsule fluid delivery device 100, whereas FIG. 1B is a conceptual diagram of human patient 10 receiving treatment to their left elbow 22 with portable joint capsule fluid delivery device 100. FIG. 2 is a conceptual block diagram of portable joint capsule fluid delivery device 100. FIG. 3 is an anatomical illustration of right knee 40 of patient 10 receiving treatment with portable joint capsule fluid delivery device 100.

Device 100 is an external medical device including a fluid outlet 128 in fluid communication with a fluid reservoir 118. Device 100 includes a fluid pump 124 configured to deliver a therapeutic fluid 120 from fluid reservoir 118 through fluid outlet 128 in response to control signals from a control module 130. Fluid reservoir 118 includes a port 119 to facilitate filling fluid reservoir 118 with therapeutic fluid 120 prior or during operation of device 100 to deliver therapeutic fluid 120 to a joint capsule of patient 10. In some example, port 119 may include a self-healing membrane accessible fillable by injection with a needle. Such examples may help preserve the sterility of therapeutic fluid 120. In the same or different examples, port 119 may include a cap or other removable cover to access fluid reservoir 118 for filling and/or cleaning.

Tubing segment 140 is in fluid communication with fluid outlet 128, fluid pump 124 and fluid reservoir 118 by way of a direct connection to fluid outlet 128. In this manner, therapeutic fluid 120 is within the portion of fluid flow path 110 including fluid pump 124 and fluid outlet 128. With its connection to fluid outlet 128, tubing segment 140 delivers therapeutic fluid 120 to a joint capsule a patient, such as right knee 40 (FIG. 1A), left elbow 22 (FIG. 1B) or other synovial joint of patient 10.

As shown in FIG. 2, device 100 further includes a fluid inlet 112, and an inlet valve 114 in fluid communication with fluid inlet 112 and fluid reservoir 118. Inlet valve 114 is configured to control fluid flow through fluid inlet 112 to replenish fluid reservoir 118 in response to control signals from a control module 130 as part of a flow path 110 through device 100. In some examples, inlet valve 114 is an inlet pump. Tubing segment 150 is in fluid communication with fluid inlet 112, inlet valve 114, and fluid reservoir 118 by way of a direct connection to fluid inlet 112. Tubing segment 150 facilitates draining the joint capsule of the patient while tubing segment 140 delivers therapeutic fluid 120 to the joint capsule. Flow path 110 continues through tubing segment 150, enters the joint capsule of a patient before returning to device 100 via through tubing segment 150 and fluid inlet 112. While therapeutic fluid 120 may be diluted with synovial fluid of a joint capsule during treatment of a patient, the replenishment of fluid reservoir 118 with flow from tubing segment 150 means that therapeutic fluid 120 may be within the entirety of fluid flow path 110 including fluid outlet 128, tubing segment 140, a joint capsule of a patient, tubing segment 150, and fluid inlet 112.

As mentioned above, control module 130 sends control signals to inlet valve 114 and fluid pump 124. Device 100 further includes fluid sensor 126, which is located between fluid pump 124 and fluid outlet 128. Fluid sensor 126 is configured to monitor therapeutic fluid 120 between fluid pump 124 and fluid outlet 128 and further configured to output sensor data corresponding to a monitored condition of therapeutic fluid 120 to control module 130. In various examples, the sensor data may include fluid pressure data and/or fluid flow rate data. Flow sensors may include optical sensors, pinwheel sensors, and others. Pressure sensors may be located outside flow path 110 and sense pressure through a membrane.

In the same or different examples, control module 130 may also determine fluid flow rates through fluid outlet 128 and fluid inlet 112 based on data communications with inlet valve 114 and fluid pump 124. For example, inlet valve 114 and/or fluid pump 124 may include a peristaltic pump or other pump such that the pump components do not come in direct contact with fluid flowing through the pump. In some examples, such as a peristaltic pump or piston pump, flow rates may be determined directly by the operation of fluid pump 124, such as directly from control signals sent to the peristaltic pump by control module 130. In the same or different examples, inlet valve 114 and/or fluid pump 124 may including sensing capabilities, and may transmit operational data and/or sensor data, such as fluid pressure data and/or fluid flow rate data, to control module 130. In specific examples, such a peristaltic pump of fluid pump 124 may include a direct current motor operable in a range of 1-20 volts, such as a range of 5-6 volts.

Based on known characteristics of the fluid flow, including sensor data from fluid sensor 126, control module 130 is configured to send control signals to operate inlet valve 114 and fluid pump 124 to circulate therapeutic fluid 120 through a joint capsule 50 of a patient 10 according to preprogrammed flow rates while maintaining a positive fluid pressure within joint capsule 50 of patient 10. For example, control module 130 may operate fluid pump 124 to maintain preset flow rate(s) and may further operate inlet valve 114 to maintain a desired pressure within a joint cavity of a patient based on fluid pressure data from fluid sensor 126. In different examples, flow rates and/or pressures may be held constant or may be adjusted over time as desired to support the efficacy of therapeutic fluid 120.

Fluid filters 116A, 116B, 116C (collectively, "filters 116") are positioned in series between inlet valve 114 and fluid reservoir 118 within flow path 110. Fluid filters 116 provide multiple stages of filtering fluid before storage within fluid reservoir 118. For example, each filter may catch progressively smaller particulates. Fluid filters 116 may catch loose bodies or other particulates flushed from a joint capsule of a patient during treatment thereby preventing reentry of injurious materials into the joint capsule. Other examples may include more or less filters at any point along flow path 110 within device. Other examples may not include filters.

In some particular examples, filters 116 may represent a staggered filter system with an upper chamber of larger filters, such as filter 116A, being negatively charged to attract procoagulative factors, whereas later filters such, as filters 116B, 116C, may be hydrophobic and arginine poor, to progressively filter smaller debris.

Device 100 further includes a light 122 operable to illuminate therapeutic fluid 120 within fluid reservoir 118.

For example, light 122 may be configured to activate and/or sanitize therapeutic fluid 120. In various examples, light 122 may include a wavelength in the red range, near infra-red range and/or blue range. Red and near infra-red wavelengths may support photobiomodulation, thereby stimulating living cells within therapeutic fluid 120 to generate more energy and undergo self-repair through the use of near infrared (NIR) light. Red and near infrared light may activate cytochrome C oxidase (CCO) in mitochondria which increases cellular adenosine triphosphate (ATP) production, potentially supporting the regenerative effects of examples of therapeutic fluid 120 that includes living cells, such as stem cells, platelet-rich plasma (PRP), mesenchymal stem cells, and/or microfragmented adipose tissue.

In contrast, blue light may have antibiotic and other antiseptic properties, thereby helping treat infections, and or preserve the sterility of therapeutic fluid 120. In some examples, blue light may have a 400-470 nanometer (nm) wavelength, such as a 400-410 nm wavelength, such as a 405 nm wavelength. Because blue light may cause burns to a patient, device 100 should include shielding to prevent projection of the light directly on to the patient. In addition, shielding may further protect other components of device 100. In some examples, fluid reservoir 118 may be formed from a translucent glass in resistant to damage from blue light, while the other components of device 100 are shielded from light 122. Such shielding may include flexible skin shielding and/or polymer shielding to mitigate injurious effects of blue light.

Device 100 further includes a coating 111 along one or more components of flow path 110. As shown, coating 111 is on an interior surface of reservoir 118. Coating 111 is configured to inhibit protein and cell adhesion within fluid flow path 110. Coating 111 may be utilized on all components of device 100 forming fluid flow path 110, such as fluid inlet 112, inlet valve 114, fluid filter 116, fluid reservoir 118, fluid pump 124, fluid sensor 126, and/or fluid outlet 128. Tubing segments 140, 150 and/or needles 141, 151 may also include coating 111. In various examples, coating 111 may include one or more of polyethylene oxide (PEO), pyrolytic carbon coating, elastin inspired polymer, aurintricarboxylic acid and/or a hydrophilic coating, such as a hydrophilic coating configured to inhibit thrombin PEG-CTI via FXIIa inhibition. In addition, or as an alternative to coating 111, the components of device 100 along flow path 110 may be formed form polymers configured to reduce platelet adhesion.

In some examples, coating 111 and/or one or more of filters 116 include proteins along artificial surfaces mediate the attachment of platelets, leukocytes, and red blood cells to artificial surfaces. Further, proteins more often adsorb to hydrophobic surfaces than hydrophilic surfaces, independent of flow. Along metallic surfaces such as titanium, blood coagulates outside the vascular system independent of low protein adsorption to or activation by surfaces, due to the absence of an active down-regulation of procoagulative processes by the vascular endothelium. However, coating 111 and/or one or more of filters 116 may be configured to reduce this procoagulative process by including materials such as, polyethylene oxide (PEO), pyrolytic carbon, elastin inspired polymer, and aurintricarboxylic acid. In addition, selected elements along flow path 110, such as filter 116A, may be negatively charged to attract procoagulative factors. Other elements along the flow path 110 may have a neutral or positive electrical charge to reduce this procoagulative process.

Device 100 further includes a user interface 104, a battery 132, a charging port 134, and a data port 136 to support the operation of device 100 in the delivery of therapeutic fluid 120 to a joint capsule of a patient. Battery 132 is configured to supply electrical power to components of device 100, such as fluid pump 124, inlet valve 114, light 122, and control module 130, whereas charging port 134 is operable to charge battery 132. In some examples, charging port 134 may also be used to directly power components of device 100. Other examples may not include a battery, in which case an external power source, such as an electrical plug may be used to power components of device 100.

User interface 104 facilitates presentation of information to a user of device 100, such as a clinician or patient 10, whereas data port 136 facilitates data transmissions with external devices. User interface 104 may facilitate programming therapy parameters, and/or transmission of information related to device 100 operations over time or in real-time. In various examples, user interface 104 may include one or more of a visible display, audible alerts, keypads or other inputs, and or connection to a personal electronic device, such as wired or wireless connection to a user's cell phone.

Similarly, data port 136 may facilitate a wired and/or wireless connection to an external device. Example wired or wireless connections include USB, Wi-Fi, Bluetooth, cellular transmissions, as well as any other transmission standards suitable to support the operations of device 100. Data port 136 may facilitate programming therapy parameters, and/or transmission of information related to device 100 operations over time or in real-time. Data port 136 may also facilitate remote monitoring and/or programming of device 100 by a clinician. In some examples, such as USB, data port 136 may be combined with charging port 134 as a unitary component.

As shown in FIG. 3, joint capsule 50 encloses the knee 40 formed by femur 42, tibia 44, and fibula 46. The patella of knee 40 is not shown. Soft tissues of knee 40 illustrated in FIG. 3 include lateral meniscus 52, medial meniscus 53, lateral collateral ligament 54, medial collateral ligament 55, anterior cruciate ligament 56, and posterior cruciate ligament 58. Treatment of knee 40 by delivering therapeutic fluid 120 with device 100 may promote healing of any of these tissues. For example, completely torn ligaments, torn or worn meniscus, worn cartilage, and arthritis may benefit from treatment utilizing device 100. In some examples, treatments with device 100 may be combined with surgical intervention to repair tissues, either before or after surgery.

FIG. 3 further illustrates a needle 141 in fluid communication with tubing segment 140. Needle 141 accesses joint capsule 50 through skin 48 to facilitate infusing joint capsule 50 with therapeutic fluid 120 via fluid outlet 128 of portable joint capsule fluid delivery device 100 and tubing segment 140. In addition, needle 151 accesses joint capsule 50 through skin 48 to facilitate draining joint capsule 50 via tubing segment 150 and fluid inlet 112 of portable joint capsule fluid delivery device 100. Fluid flow path 110 includes tubing segment 140, needle 141, joint capsule 50, needle 151, and tubing segment 150. As discussed previously, fluid flow path 110 further includes recirculating flow through portable joint capsule fluid delivery device 100. While not shown, needles 141, 151 may be secured with bandages or tape, and the entry points of needles 141, 151 through skin 48 of patient 10 may likewise be covered with bandages, wraps and/or antiseptics to maintain a sterile environment.

In both FIG. 1A and FIG. 1B, device 100 is secured to a limb of patient 10 with straps 102. Specifically, with respect to FIG. 1A, device 100 is secured to the front of thigh 32 of right leg 30, and with respect to FIG. 1B, device 100 is secured to the side of right left arm 20 above left elbow 22. These positions are merely examples and other positions may be selected by a clinician and their patient for comfort during treatment of patient 10 with device 100.

While device 100 is secured with straps 102, the treated joint remains mobile. In some cases, a clinician may immobilize the joint during treatment of the joint with device 100. In other examples, the clinician may prescribe movement of the joint during treatment of the joint with device 100, for example to support the removal of loose bodies with fluid flow created by device 100 through the joint capsule.

The portability of device 100 allows patient 10 to receive treatment of device 100 outside of a clinical setting. The mobility afforded patient 10 may allow for long-term treatment with device 100, such as 4, 6, 8, or 12 hours per day, with a reduced impact on daily activity of patient 10. For example, a prescribed treatment of the joint of the patient may include operation of device 100 for a number of hours per day every day any number of days, such as 3 days, 7 days, or even weeks.

Any number of therapeutic fluids may be used in combination with device 100 according to the needs of patient 10. In various examples, therapeutic fluid 120 may include living cells to support natural regeneration of patient tissues with a joint capsule, such as, but not limited to stem cells, platelet-rich plasma (PRP), mesenchymal stem cells, and/or microfragmented adipose tissue (MFAT). In the same or different examples, therapeutic fluid 120 may include lubricants, such as Wharton's jelly. In the same or different examples, therapeutic fluid 120 may include fluids to support flushing a joint capsule, which may help remove loose bodies. Such flushing fluids may include saline, hypertonic saline, and/or hyperosmolar sugar solution. In the same or different examples, therapeutic fluid 120 may include components to sterilize and/or treat infections within a joint capsule, such as hydrogen peroxide, povidone-iodine, and/or antibiotics. In the same or different examples, therapeutic fluid 120 may include any number of pharmaceuticals to support treatment of the joint of a patient, including but not limited to, painkillers, steroids, antiseptics, and others.

As these examples illustrate, device 100 may be combined with any number of available therapeutic fluids to support the treatment of a joint capsule. The portability of device 100 allows such treatments to occur for longer periods of time than procedures occurring within a clinical setting, such as injections or flushing. Extending period of time therapeutic fluids are delivered to a joint capsule may improve the efficacy of the therapeutic fluids by other means.

Figure 4:
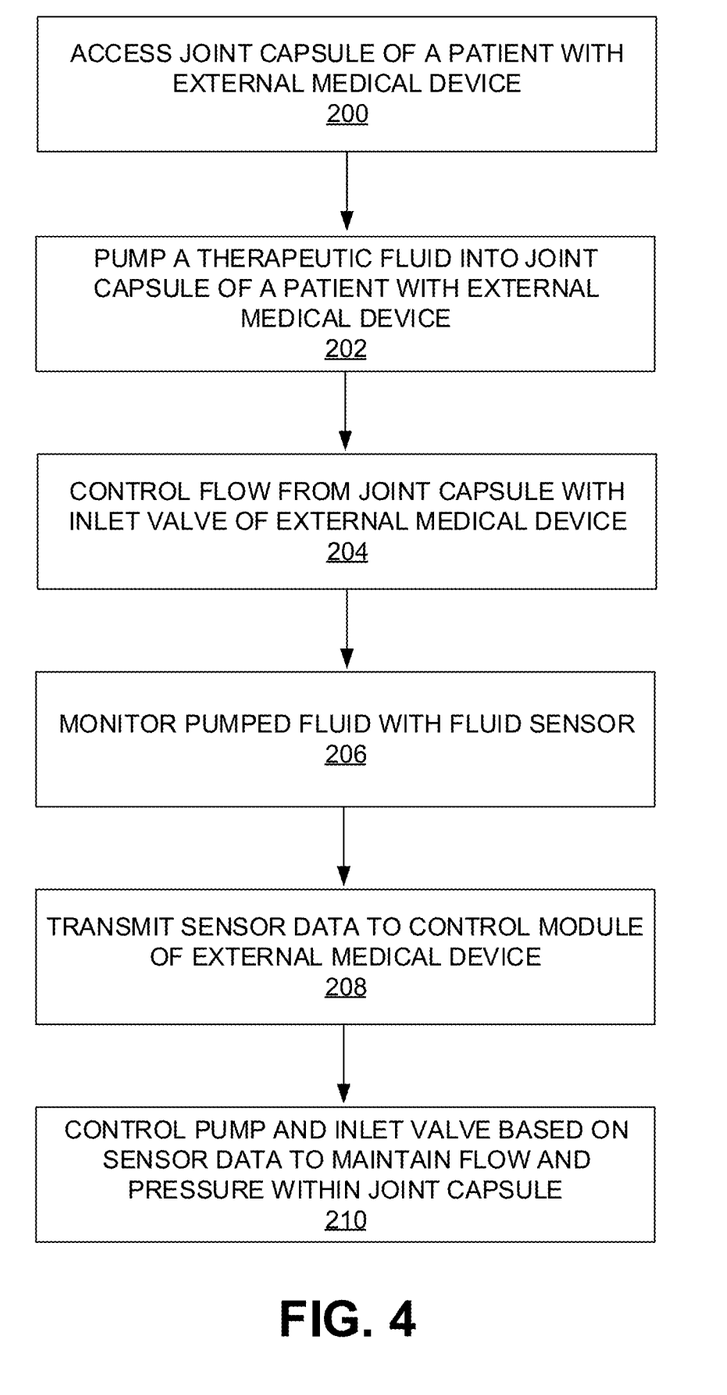
FIG. 4 is a flowchart illustrating a method for delivering fluid to a joint capsule of a patient.

FIG. 4 is a flowchart illustrating a method 200 for delivering fluid to a joint capsule of a patient. For clarity, the techniques of FIG. 4 are described with respect to portable joint capsule fluid delivery device 100 and right knee 40 of patient 10, although the techniques may likewise be applied to other joints, such as left elbow 22 of patient 10, and to variations of the joint capsule fluid delivery devices disclosed herein.

First, a user, such as a clinician or a patient, accesses a joint capsule of a patient to fluidly connect fluid inlet 112 and fluid outlet 128 of device 100 (200). For example, a clinician may first disinfect skin 48 using a common disinfectant, such as a solution including alcohol, iodine and/or chloraprep. Next, the clinician may insert needles 141, 151 to access joint capsule 50. For example, examples, needles 141, 151 may be relatively large, such as 14 gauge, (1.6 millimeters (mm) internal diameter) to facilitate therapy, such as flushing and removal of loose bodies from within joint capsule 50. In some examples, the clinician may utilize an imaging system, such as ultrasound, to assist in the proper placement of needles 141, 151. In some further examples, a catheter or stent, such as an expandable stent, may be used to increase the diameter of the access into joint capsule 50 beyond that provided by needles 141, 151, such as to a diameter of at least 4 mm, such as to a range of 6 mm to 8 mm. In such examples, the stent or catheter may remain in place during the delivery of therapeutic fluid 120 by device 100 in lieu of needles 141, 151 within the flow path 110 to maintain a larger access to joint capsule 50.

Following the access to joint capsule 50 with needles 141, 151 and/or a larger stent or catheter, device 100 is operated to begin therapy. In particular, control module 130 actives fluid pump 124 to pump therapeutic fluid 120 from fluid reservoir 118 into joint capsule 50 of patient 10 via fluid outlet 128 and tubing segment 140 (202) according to control signals from control module 130. Tubing segments 140, 150 and stents or catheters in lieu of needles 141, 151 may provide a relatively large diameter, such as 1 centimeter or more, such as 1.6 centimeters in order to facilitate a desired flow rate with a limited pressure drop through tubing segments 140, 150. For example, a flow rate may be at least 1 milliliter per second, such as within a range of 2-3 milliliters per second.

During the delivery of therapeutic fluid 120 to joint capsule 50, control module 130 controls flow from joint capsule 50 via a tubing segment 150 with inlet valve 114 (204). Fluid inlet 112 is in fluid communication with fluid reservoir 118 such that flow through fluid inlet 112 replenishes fluid reservoir 118. The fluid flowing through fluid inlet 112 may include therapeutic fluid 120 which has passed through joint capsule 50, although the original concentration of therapeutic elements within therapeutic fluid 120 may be diluted with bodily fluids, such as synovial fluid. Filters 116 filter fluid flowing through inlet 112 before entering fluid reservoir 118. In other examples, filters 116 may be positioned within a different location of flow path 110 between fluid inlet 112 and fluid outlet 128. Also, during the delivery of therapeutic fluid 120 to joint capsule 50, fluid sensor 126 monitoring a condition of therapeutic fluid 120 between fluid pump 124 and fluid outlet 128 fluid sensor 126 (206). Fluid sensor 126 further transmits sensor data based on monitored condition of therapeutic fluid 120 control module 130 (208).

Based on the sensor data from fluid sensor 126, control module 130 sends fluid inlet control signals to inlet valve 114 and fluid outlet control signals to fluid pump 124 to circulate therapeutic fluid 120 through joint capsule 50 of patient 10. The control signals may correspond to preprogrammed flow rates while maintaining a positive fluid pressure within joint capsule 50 of patient 10 (210). For example, control module 130 may restrict flow through inlet valve 114 to maintain a pressure of 20-80 mm of mercury (mmHg), such as pressure of about 40 mmHg.

Device 100 may be programed to provide any number of flow rates and pressures over time. In one example, device 100 may operate fluid pump 124 to circulate therapeutic fluid 120 through joint capsule 50 continuously or near continuously over a period of time, such as 4-12 hours, such as 8 hours. Light 122 may be activated during this time to sterilize and/or activate fluid circulating through device 100. Fluid pumped into joint capsule 50 through tube segment 140 may drain through tube segment 150 at approximately the same flow rate as fluid is pumped into joint capsule 50. In some examples, inlet valve 114 may be operated to maintain a positive pressure within joint capsule 50. In other examples, inlet valve 114 may be completely open in order to not restrict flow. In yet further examples, inlet valve 114 may include a pump, such as a peristaltic pump, to create a negative pressure and draw fluids through tube segment 150.

In other examples, device 100 may operate fluid pump 124 to inflate joint capsule 50 with therapeutic fluid 120. Once operation of fluid pump 124 creates a desired pressure and/or volume fluid pump 124 may cease pumping. After a set period of time, such as 1 hour, inlet valve 114 may open to drain excess fluid from joint capsule 50.

Figure 5:
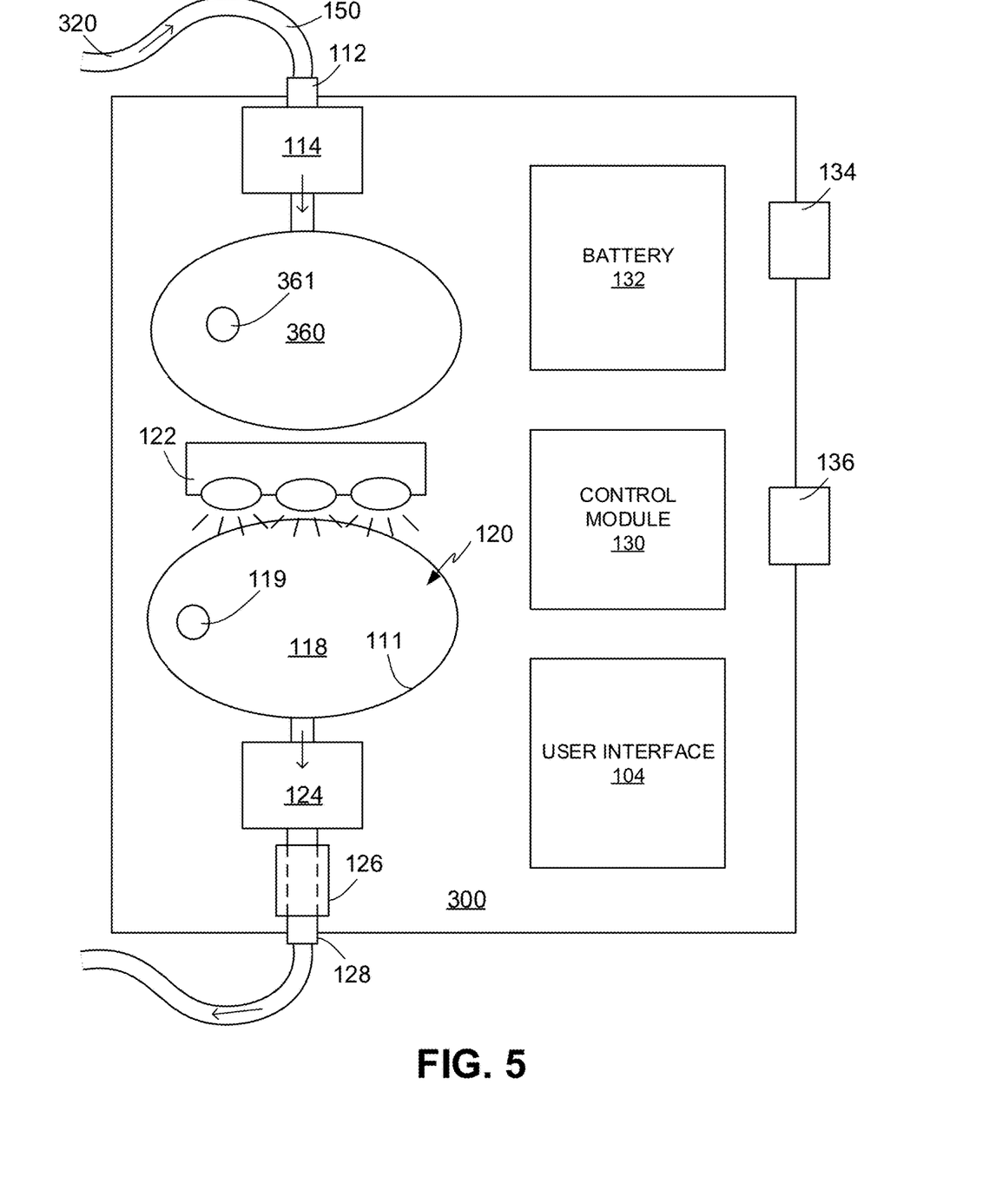
FIG. 5 is a conceptual block diagram of a portable joint capsule fluid delivery device in an alternative configuration as compared to the portable joint capsule fluid delivery device of FIG. 2.

FIG. 5 is a conceptual block diagram of a portable joint capsule fluid delivery device 300, which provides an alternative configuration as compared to portable joint capsule fluid delivery device 100. In contrast to portable joint capsule fluid delivery device 100, portable joint capsule fluid delivery device 300 does not recirculate fluid through device 300. Instead, device 300 includes an internal drainage vessel 360 in fluid communication with fluid inlet 112. Drainage vessel 360 receives drainage fluid 320 from a joint capsule, such as joint capsule 50. Drainage vessel 360 separate from fluid reservoir 118 such that drainage fluid 320 does not mix with therapeutic fluid within fluid reservoir 118. Drainage vessel 360 includes a drain 361 to facilitate removal of drainage fluid 320. In all other aspects, portable joint capsule fluid delivery device 300 is functionally the same as portable joint capsule fluid delivery device 100, and the variations and techniques described with respect to device 100 are equally applicable to device 300. For brevity, additional details included in the description of portable joint capsule fluid delivery device 100 are not repeated with respect to portable joint capsule fluid delivery device 300.

In other examples, a drainage vessel and/or fluid reservoir may be external to a housing of device 300. For example, an external drainage vessel and an external fluid reservoir may connect to device 300 by way of tubular connections to inlet valve 114 and fluid pump 124 respectively.

The specific techniques delivering therapeutic fluid to a joint capsule of a patient, such as portable joint capsule fluid delivery devices 100, 300 are merely illustrative of the general inventive concepts included in this disclosure as defined by the following claims. As an example, this disclosure applies not only portable joint capsule fluid delivery devices, but also to larger joint capsule fluid delivery devices, including those with external fluid reservoirs, external drainage vessels and/or stationary power sources, such as a plug configured to connect to a standard electrical outlet.

The invention claimed is:

1. An external medical device comprising:
a wearable housing including a housing wall;
a fluid inlet traversing the housing wall;
an inlet control device within the housing, the inlet control device in fluid communication with the fluid inlet to control fluid flow through the fluid inlet in response to fluid inlet control signals,
wherein the inlet control device is an inlet valve or an inlet pump;
a fluid outlet traversing the housing wall in fluid communication with a fluid reservoir, wherein the fluid reservoir is in fluid communication with the fluid inlet such that fluid flow through the fluid inlet replenishes the fluid reservoir;
a fluid pump within the housing, the fluid pump configured to deliver a therapeutic fluid from the fluid reservoir through the fluid outlet in response to fluid outlet control signals;
a fluid sensor within the housing, the fluid sensor configured to monitor the therapeutic fluid between the fluid pump and the fluid outlet and further configured to output sensor data corresponding to a monitored condition of the therapeutic fluid; and
a control module configured to receive the sensor data and output, based on the sensor data, the fluid inlet control signals to the inlet control device and the fluid outlet control signals to the fluid pump.

2. The external medical device of claim 1, further comprising:
a first tubing segment in fluid communication with the fluid outlet;
a first needle in fluid communication with the first tubing segment, the first needle being configured to access a joint capsule of a patient to facilitate infusing the joint capsule with the therapeutic fluid via the fluid outlet and the first tubing segment;
a second tubing segment in fluid communication with the fluid inlet; and
a second needle in fluid communication with the second tubing segment, the second needle being configured to access the joint capsule of the patient to facilitate draining the joint capsule via the second tubing segment and the fluid inlet.

3. The external medical device of claim 1, further comprising a fluid filter within a flow path within the housing between the fluid inlet and the fluid outlet.

4. The external medical device of claim 1, wherein the control module is configured to operate the inlet control device and the fluid pump to circulate the therapeutic fluid through a joint capsule of a patient according to preprogrammed flow rates while maintaining a positive fluid pressure within the joint capsule of the patient.

5. The external medical device of claim 1, wherein the sensor data includes one or more of a group consisting of:
fluid pressure data; and
fluid flow rate data.

6. The external medical device of claim 1, further comprising the therapeutic fluid within a flow path including the fluid pump and the fluid outlet, wherein the therapeutic fluid includes one or more of a group consisting of:
platelet-rich plasma (PRP);
mesenchymal stem cells; and
microfragmented adipose tissue (MFAT).

7. The external medical device of claim 1, further comprising the therapeutic fluid within a flow path including the fluid pump and the fluid outlet, wherein the therapeutic fluid includes one or more of a group consisting of:
Wharton's jelly;
saline;
hypertonic saline;
hyperosmolar sugar solution;
hydrogen peroxide;
povidone-iodine; and
antibiotics.

8. The external medical device of claim 1, further comprising a coating configured to inhibit protein and cell adhesion within a flow path within the housing, the flow path including the fluid pump and the fluid outlet.

9. The external medical device of claim 1, wherein the inlet control device is the inlet pump.

10. The external medical device of claim 1, further comprising a battery within the housing, the battery configured to supply electrical power to the fluid pump, the inlet control device, and the control module.

11. The external medical device of claim 1, wherein the inlet control device is the inlet valve.

12. The external medical device of claim 1, the external medical device of claim 1, further comprising a strap configured to secure the housing to a limb of a patient while allowing the patient to remain mobile.

13. An external medical device comprising:
a fluid inlet;
an inlet control device in fluid communication with the fluid inlet to control fluid flow through the fluid inlet in response to fluid inlet control signals,
wherein the inlet control device is an inlet valve or an inlet pump;
a fluid reservoir, wherein the fluid reservoir is in fluid communication with the fluid inlet such that fluid flow through the fluid inlet replenishes the fluid reservoir;
a fluid outlet in fluid communication with the fluid reservoir;
a fluid pump configured to deliver a therapeutic fluid from the fluid reservoir through the fluid outlet in response to fluid outlet control signals;
a fluid pressure sensor located outside a flow path of the therapeutic fluid and configured to monitor the therapeutic fluid through a membrane between the fluid pump and the fluid outlet and further configured to output sensor data corresponding to a monitored condition of the therapeutic fluid; and
a control module configured to receive the sensor data and output, based on the sensor data, the fluid inlet control signals to the inlet control device and the fluid outlet control signals to the fluid pump.

14. The external medical device of claim 13, further comprising a light illuminating the therapeutic fluid within the fluid reservoir, the light being configured to activate and/or sanitize the therapeutic fluid.

15. The external medical device of claim 14, wherein the light includes a wavelength of a group consisting of:
near-infrared; and
blue.

16. The external medical device of claim 13, further comprising a port traversing the housing, the port with a self-healing membrane to facilitate filling the fluid reservoir with the therapeutic fluid.

17. An external medical device comprising:
a wearable housing including a housing wall;
a fluid reservoir within the housing;
a fluid outlet traversing the housing wall, the fluid outlet in fluid communication with the fluid reservoir;
a fluid pump within the housing, the fluid pump configured to deliver a therapeutic fluid from the fluid reservoir through the fluid outlet in response to fluid outlet control signals;
a fluid inlet traversing the housing wall;
an inlet control device within the housing, the inlet control device in fluid communication with the fluid inlet and the fluid reservoir, the inlet control device being configured to control fluid flow through the fluid inlet to replenish the fluid reservoir in response to fluid inlet control signals,
wherein the inlet control device is an inlet valve or an inlet pump;
a fluid filter within the housing and within a flow path between the fluid inlet and the fluid outlet;
a fluid sensor within the housing, the fluid sensor configured to monitor the therapeutic fluid between the fluid pump and the fluid outlet and further configured to output sensor data corresponding to a monitored condition of the therapeutic fluid;
a control module configured to receive the sensor data and output, based on the sensor data, the fluid inlet control signals to the inlet control device and the fluid outlet control signals to the fluid pump;
a first tubing segment in fluid communication with the fluid outlet;
a first needle in fluid communication with the first tubing segment, the first needle being configured to access a joint capsule of a patient to facilitate infusing the joint capsule with the therapeutic fluid via the fluid outlet and the first tubing segment;
a second tubing segment in fluid communication with the fluid inlet; and
a second needle in fluid communication with the second tubing segment, the second needle being configured to access the joint capsule of the patient to facilitate draining the joint capsule via the second tubing segment and the fluid inlet.

18. The external medical device of claim 17, further comprising a light within the housing, the light configured to illuminate the therapeutic fluid within the fluid reservoir, the light being configured to activate and/or sanitize the therapeutic fluid.

19. The external medical device of claim 17, wherein the control module is configured to operate the inlet control device and the fluid pump to circulate the therapeutic fluid through the joint capsule of the patient according to preprogrammed flow rates while maintaining a positive fluid pressure within the joint capsule of the patient.

20. The external medical device of claim 17, further comprising a coating configured to inhibit protein and cell adhesion within the flow path.

21. The external medical device of claim 17, further comprising a battery within the housing, the battery configured to supply electrical power to the fluid pump, the inlet control device, and the control module.

22. The external medical device of claim 1, the external medical device of claim 17, further comprising a strap configured to secure the housing to a limb of the patient while allowing the patient to remain mobile.

\* \* \* \* \*